United States Patent
Kim et al.

(10) Patent No.: US 11,078,206 B2
(45) Date of Patent: Aug. 3, 2021

(54) AMINO-FLUOROPIPERIDINE DERIVATIVES AS KINASE INHIBITOR

(71) Applicant: Daewoong Pharmaceutical Co., Ltd., Gyeonggi-do (KR)

(72) Inventors: In Woo Kim, Seoul (KR); Seung Hwarn Jeong, Daejeon (KR); Nam Youn Kim, Gyeonggi-do (KR); Jun Hee Lee, Seoul (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/770,642

(22) PCT Filed: Dec. 28, 2018

(86) PCT No.: PCT/KR2018/016812
§ 371 (c)(1),
(2) Date: Jun. 8, 2020

(87) PCT Pub. No.: WO2019/132560
PCT Pub. Date: Jul. 4, 2019

(65) Prior Publication Data
US 2020/0299298 A1 Sep. 24, 2020

(30) Foreign Application Priority Data
Dec. 28, 2017 (KR) .................. 10-2017-0183060

(51) Int. Cl.
C07D 487/04 (2006.01)
A61P 37/00 (2006.01)
A61P 35/00 (2006.01)

(52) U.S. Cl.
CPC ............ C07D 487/04 (2013.01); A61P 35/00 (2018.01); A61P 37/00 (2018.01)

(58) Field of Classification Search
CPC .................................................. C07D 487/04
See application file for complete search history.

(56) References Cited

U.S. PATENT DOCUMENTS

| 9,040,547 | B2 | 5/2015 | Cheng et al. |
| 9,840,517 | B2 | 12/2017 | Liu et al. |
| 2012/0094999 | A1 | 4/2012 | Gray et al. |
| 2013/0079324 | A1 | 3/2013 | Cheng et al. |
| 2015/0158864 | A1 | 6/2015 | Thorarensen et al. |
| 2015/0203502 | A1 | 7/2015 | Cheng et al. |
| 2016/0229865 | A1 | 8/2016 | Liu et al. |
| 2017/0247372 | A1 | 8/2017 | Thorarensen et al. |
| 2018/0051036 | A1 | 2/2018 | Liu et al. |
| 2019/0040065 | A1 | 2/2019 | Gray et al. |
| 2020/0317673 | A1 | 10/2020 | Kim et al. |

FOREIGN PATENT DOCUMENTS

| EA | 201490673 A1 | 6/2014 |
| KR | 2012-0047208 A | 5/2012 |
| KR | 2014-0059246 A | 5/2014 |
| KR | 2016-0054014 A | 5/2016 |
| KR | 2016-0092012 A | 8/2016 |
| KR | 20180137057 A | 12/2018 |
| RU | 2714206 C1 | 2/2020 |
| WO | WO-02/096909 A1 | 12/2002 |
| WO | WO-2010/009342 A2 | 1/2010 |
| WO | WO-2010/129053 A2 | 11/2010 |
| WO | WO-2014/025486 A1 | 2/2014 |
| WO | WO-2015/039612 A1 | 3/2015 |
| WO | WO-2015/083028 A1 | 6/2015 |
| WO | WO-2018/004306 A1 | 1/2018 |

OTHER PUBLICATIONS

Pinedo et al. (2000).*
McMahon et al. (2000).*
Zhou et al., "Discovery of Selective Irreversible Inhibitors for EGFR-T790M", Bioorganic & Medicinal Chemistry Letters, vol. 21, 2011, pp. 638-643.
D'Aura et al., "Tyrosine Kinases as Targets for the Treatment of Rheumatoid Arthritis", Nature Reviews Rheumatology, vol. 5, Jun. 2009, pp. 317-324.
Peter Norman, "Selective JAK Inhibitors in Development for Rheumatoid Arthritis", Expert Opin Investig Drugs, vol. 8, Aug. 23, 2014, 11 pages.
Whang et al., "Bruton's Tyrosine Kinase Inhibitors for the Treatment of Rheumatoid Arthritis", Drug Discovery Today, vol. 8, Aug. 19, 2014, 8 pages.
Office Action in RU Application No. 2020124577 dated Nov. 20, 2020, 19 pages.
Extended European Search Report in EP Application No. 18894845.9 dated May 11, 2021, 8 pages.
Planken et al., "Discovery of N-((3R,4R)-4-Fluoro-1-(6-((3-methoxy-1-methyl-1H-pyrazol-4-yl)amino)-9-methyl-9H-purin-2-yl)pyrrolidine-3-yl)acrylamide (PF-06747775) Through Structure-Based Drug Design: A High Affinity Irreversible Inhibitor Targeting Oncogenic EGFR Mutants with Selectivity Over Wild-Type EGFR", Journal of Medicinal Chemistry, vol. 60, No. 7, Mar. 29, 2017, pp. 3002-3019.
Office Action, Singapore Patent Application No. 11202004918X, dated Apr. 29, 2021.

* cited by examiner

*Primary Examiner* — Paul V Ward
(74) *Attorney, Agent, or Firm* — Marshall, Gerstein & Borun LLP

(57) ABSTRACT

The present invention relates to a compound represented by the following Chemical Formula 1, or a pharmaceutically acceptable salt thereof, and the compound according to the present invention can be usefully used for the prevention or treatment of diseases which are associated with kinase inhibitory actions.

6 Claims, No Drawings

AMINO-FLUOROPIPERIDINE DERIVATIVES AS KINASE INHIBITOR

TECHNICAL FIELD

The present invention relates to an amino-fluoropiperidine derivative having kinase inhibitory activity, a process for preparing the same and use thereof.

BACKGROUND ART

Protein kinase is an enzyme that catalyzes phosphorylation of specific residues of other proteins, and plays an important role in signal-transduction pathways that transduce extracellular signals to the nucleus. Further, it is involved in various diseases in vivo. In the onset or development of inflammatory disease, autoimmune disease, proliferative disease or hyperproliferative disease, and/or immunity mediated disease, there is various evidence that T-cells (or T-lymphocytes) and B-cells (or B-lymphocytes) play an important role.

Janus kinase (hereinafter referred to as "JAK") is a cytoplasmic protein tyrosine kinase that plays pivotal roles in regulating cell function in the lympho-hematopoietic system. Cytokines are known to play an important role in regulating inflammation, immunity and normal cell function, and JAK activates STAT (Signal Transducer and Activators of Transcription) proteins through tyrosine phosphorylation to provide rapid signaling pathways to cytokines. JAK/STAT signaling is known to be associated with allergies, asthma, autoimmune diseases (e.g., transplant rejection, rheumatoid arthritis, amyotrophic lateral sclerosis, multiple sclerosis etc.), solid cancers, blood cancers (e.g., leukemia, lymphoma and so on).

The JAK family is classified into four members: JAK 1, JAK 2, JAK 3, and TYK 2. Members of the JAK family pair with each other to mediate signals from a variety of cytokines. It includes JAK2 and JAK1 associated with hematopoietic growth factor signaling, and a combination of TYK2 and JAK2 is important for interferon signaling and contributes to host tolerance. JAK2 can induce anemia, thrombocytopenia, leukopenia, especially when it is involved in the hematopoietic growth factor signaling and causes excessive inhibition.

The expression of JAK1, JAK2, and TYK2 was found to be widely distributed, whereas the expression of JAK3 was restricted to lymphocytes and is associated with signaling for the common gamma chains, members of IL-2, IL-4, IL-7, IL-9, IL-15 and IL-21 receptors, particularly the common gamma chain of the IL-2 family. As soon as the cytokine is bound, the receptor carries adjacent JAK3 nearby, which induces autophosphorylation of the β-chain C-terminus. As a result, it causes activation of the STAT protein, which is an important step in retransmitting the signal to the nucleus. JAK3 controls the signal pathways of various cytokines through this process. This makes JAK3 as an attractive target for immunosuppression.

B cells play an important role in the development of autoimmune and/or inflammatory diseases. Protein-based therapeutic agents that reduce B cells, for example Rituxan, are effective in autoantibody-induced inflammatory diseases such as rheumatoid arthritis. Thus, protein kinase inhibitors that play a role in B cell activation are useful therapeutic agents for the treatment of B cell-mediated diseases, for example, for the production of autoantibodies.

Signal transduction through B cell receptor (BCR) regulates various B cell responses, including proliferation and differentiation into mature antibody-producing cells. BCR is an important regulatory element of B cell activity, and abnormal signal transduction can cause the formation of pathogenic autoantibodies leading to a plurality of autoimmune and/or inflammatory diseases and the proliferation of deregulated B cell.

Bruton's tyrosine kinase (hereinafter, referred to as "BTK") is an important regulator of the development, activation, signaling and survival of B-cells. BTK is involved in signal transduction pathways initiated by binding various extracellular ligands to their cell surface receptors. Following ligation of the B cell antigen receptor (BCR), the activity of BTK by the coincident action of the protein tyrosine kinases Lyn and Syk is required for the induction of the phospholipase C-γ2-mediated calcium mobilization. Therefore, inhibition of BTK can be a useful therapeutic approach in blocking the onset process of B-cell mediated diseases.

As mentioned above, Janus kinase and TEC-based kinases play an important role in the activation of T-cells and/or B-cells involved in the development of inflammatory diseases, autoimmune diseases, proliferative diseases or hyperproliferative diseases, and immunity mediated diseases. Therefore, the development of substances that effectively inhibit these diseases can be useful as a related therapeutic agent. Specific examples of the diseases which can be treated and prevented include cancer, transplant rejection, multiple sclerosis, rheumatoid arthritis, psoriatic arthritis, psoriasis, asthma, allergic dermatitis, atopic dermatitis, eczema, type I diabetes, diabetic complication, ulcerative colitis, Crohn's disease, autoimmune thyroid disorder, systemic depilation, Sjogren's syndrome and the like.

JAK3 kinase inhibitor, tofacitinib (CP-690550) (Pfizer Inc.) is currently approved and marketed for the treatment of rheumatoid arthritis. In addition, a BTK kinase inhibitor, ibrutinib (PCI-32765) (Pharmacyclics) is in a clinical stage, but severe side effects such as skin rash and diarrhea have been reported in clinical cases. Thus, there is a need to develop a more stable and effective substance that inhibits JAK and/or BTK (see, Nat Rev Rheumatol. 2009 Jun. 5(6) 317-24; Expert Opin Investig Drugs. 2014 Aug. 23(8) 1067-77; Drug Discov Today 2014 Aug. 19(8) 1200-4; WO2002/096909; WO2010-009342).

Therefore, the present inventors have found a new amino-fluoropiperidine derivative having an excellent inhibitory activity as a kinase inhibitor, thereby completing the present invention.

DETAILED DESCRIPTION OF THE INVENTION

Technical Problem

It is an object of the present invention to provide an amino-fluoropiperidine derivative having an inhibitory ability against kinase, particularly tyrosine kinase, a process for preparing the same and use thereof.

It is another object of the present invention to provide a pharmaceutical composition comprising the amino-fluoropiperidine derivative as an active ingredient.

Technical Solution

In order to achieve the above objects, a compound represented by the following Chemical Formula 1, or a pharmaceutically acceptable salt thereof is provided herein:

[Chemical Formula 1]

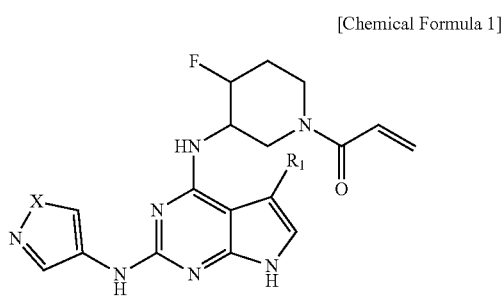

wherein, in Chemical Formula 1,
$R_1$ is $C_{1-5}$ alkyl, halogen, or cyano,
X is N—$R_2$, O, or S,
$R_2$ is $C_{1-5}$ alkyl, $C_{1-5}$ haloalkyl, or $C_{3-6}$ cycloalkyl.

Preferably, $R_1$ is methyl, ethyl, propyl, isopropyl, butyl, isobutyl, pentyl, isopentyl, neopentyl, bromo, chloro, fluoro, or cyano.

Preferably, $R_2$ is methyl, ethyl, propyl, isopropyl, butyl, isobutyl, pentyl, isopentyl, neopentyl, fluoromethyl, difluoromethyl, trifluoromethyl, 2-fluoroethyl, 2,2-difluoroethyl, 2,2,2-trifluoroethyl, cyclopropyl, cyclobutyl, cyclopentyl, or cyclohexyl.

Representative examples of the compound represented by the Chemical Formula 1 are as follows:

1) 1-((3S,4R)-3-(5-chloro-2-(1-ethyl-1H-pyrazol-4-ylamino)-7H-pyrrolo[2,3-d]pyrimidin-4-ylamino)-4-fluoropiperidin-1-yl)prop-2-en-1-one,
2) 1-((3S,4R)-3-(5-chloro-2-(1-(2,2-difluoroethyl)-1H-pyrazol-4-ylamino)-7H-pyrrolo[2,3-d]pyrimidin-4-ylamino)-4-fluoropiperidin-1-yl)prop-2-en-1-one,
3) 1-((3S,4R)-3-(5-chloro-2-(1-cyclopropyl-1H-pyrazol-4-ylamino)-7H-pyrrolo[2,3-d]pyrimidin-4-ylamino)-4-fluoropiperidin-1-yl)prop-2-en-1-one,
4) 1-((3S,4R)-3-(5-chloro-2-(isoxazol-4-ylamino)-7H-pyrrolo[2,3-d]pyrimidin-4-ylamino)-4-fluoropiperidin-1-yl)prop-2-en-1-one,
5) 1-((3S,4R)-3-(5-chloro-2-(isothiazol-4-ylamino)-7H-pyrrolo[2,3-d]pyrimidin-4-ylamino)-4-fluoropiperidin-1-yl)prop-2-en-1-one,
6) 4-((3S,4R)-1-acryloyl-4-fluoropiperidin-3-ylamino)-2-(1-ethyl-1H-pyrazol-4-ylamino)-7H-pyrrolo[2,3-d]pyrimidine-5-carbonitrile,
7) 4-((3S,4R)-1-acryloyl-4-fluoropiperidin-3-ylamino)-2-(1-(2,2-difluoroethyl)-1H-pyrazol-4-ylamino)-7H-pyrrolo[2,3-d]pyrimidine-5-carbonitrile,
8) 4-((3S,4R)-1-acryloyl-4-fluoropiperidin-3-ylamino)-2-(1-cyclopropyl-1H-pyrazol-4-ylamino)-7H-pyrrolo[2,3-d]pyrimidine-5-carbonitrile,
9) 4-((3S,4R)-1-acryloyl-4-fluoropiperidin-3-ylamino)-2-(isoxazol-4-ylamino)-7H-pyrrolo[2,3-d]pyrimidine-5-carbonitrile,
10) 1-((3S,4R)-3-(2-(1-ethyl-1H-pyrazol-4-ylamino)-5-methyl-7H-pyrrolo[2,3-d]pyrimidin-4-ylamino)-4-fluoropiperidin-1-yl)prop-2-en-1-one,
11) 1-((3S,4R)-4-fluoro-3-(2-(isoxazol-4-ylamino)-5-methyl-7H-pyrrolo[2,3-d]pyrimidin-4-ylamino)piperidin-1-yl)prop-2-en-1-one, and
12) 1-((3S,4S)-3-(5-chloro-2-(1-ethyl-1H-pyrazol-4-ylamino)-7H-pyrrolo[2,3-d]pyrimidin-4-ylamino)-4-fluoropiperidin-1-yl)prop-2-en-1-one.

In addition, the compounds of the present invention may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1 whose concentration has effective action because it is relatively non-toxic and harmless to the patients and whose side effects do not degrade the beneficial efficacy of the above compound.

Pharmaceutically acceptable salts can be obtained by conventional methods using inorganic or organic acids. For example, the pharmaceutically acceptable salt can be prepared by dissolving the compound represented by Chemical Formula 1 in a water-miscible organic solvent, e.g., acetone, methanol, ethanol or acetonitrile, followed by adding an organic acid or an inorganic acid, and filtering and drying the precipitated crystals. Alternatively, it may be prepared by subjecting a solvent or an excessive amount of acid from the acid-added reaction mixture to reduced pressure and then drying the residue, or by adding a different organic solvent and then filtering the precipitated salt. At this time, the preferred salts may include salts derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid or toluenesulfonic acid, and the like.

A pharmaceutically unacceptable salt or solvate of the compound of Chemical Formula 1 may be used as an intermediate in the production of the compound of Chemical Formula 1, or the pharmaceutically acceptable salt or the solvate thereof.

The compound of Chemical Formula 1 according to the present invention includes not only pharmaceutically acceptable salts thereof, but all solvates and hydrates that may be prepared therefrom, and includes all possible stereoisomers as well. The solvate, the hydrate and the stereoisomer of the compound represented by Chemical Formula 1 may be prepared and used from the compound of Chemical Formula 1 using common methods.

In addition, the compound represented by Chemical Formula 1 according to the present invention may be prepared either in a crystalline form or in a non-crystalline form, and when the compound represented by Chemical Formula 1 is prepared in a crystalline form, it may be optionally hydrated or solvated. In the present invention, the compound represented by Chemical Formula 1 may not only include a stoichiometric hydrate, but include a compound containing various amounts of water. The solvate of the compound represented by Chemical Formula 1 according to the present invention includes both stoichiometric solvates and non-stoichiometric solvates.

Furthermore, as an example, the present invention may produce the compound represented by Chemical Formula 1 through Reaction Scheme 1 below.

[Reaction Scheme 1]

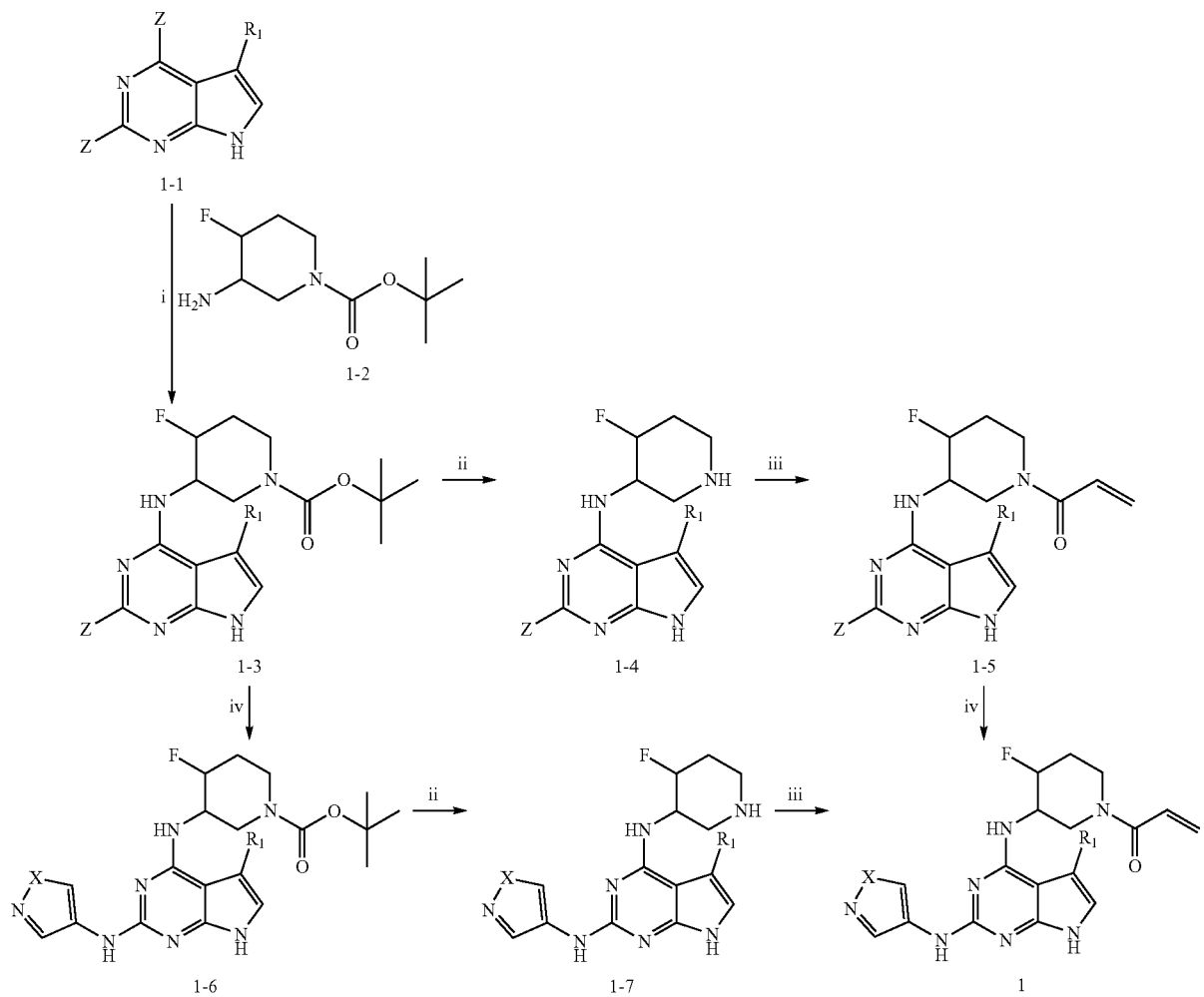

(in Reaction Scheme 1, R₁ and X are as previously defined, Z is halogen, and preferably Z is chloro)

Step i is a step of preparing a compound represented by Chemical Formula 1-3 by reacting a compound represented by Chemical Formula 1-1 with a compound represented by Chemical Formula 1-2. The reaction is preferably carried out at room temperature to high temperature in the presence of diisopropylethylamine, and the solvent is preferably ethanol.

Step ii is a reaction for removing the protecting group of the compound represented by Chemical Formula 1-3, which is a step for preparing the compound represented by Chemical Formula 1-4. The reaction is preferably carried out in the presence of hydrochloric acid (preferably, 6N hydrochloric acid), and the solvent is preferably methanol.

Step iii is a step of preparing a compound represented by Chemical Formula 1-5 by reacting a compound represented by Chemical Formula 1-4 with acyl chloride. The reaction is preferably carried out at −20° C. to 0° C. in the presence of triethylamine or sodium hydrogen carbonate. Further, the solvent is preferably a mixture of dichloromethane or tetrahydrofuran and water.

Step iv is a step of preparing a compound represented by Chemical Formula 1 by reacting a compound represented by Chemical Formula 1-5 with an amine. The reaction is preferably carried out at high temperature in the presence of trifluoroacetic acid, and the solvent is preferably 2-butanol.

Further, as shown in the Reaction Scheme 1, a compound represented by Chemical Formula 1-3, a compound represented by Chemical Formula 1-6, a compound represented by Chemical Formula 1-7, and a compound represented by Chemical Formula 1 may also be prepared in this order, and each step iv, ii, and iii is the same as described above, except for the reactants.

According to another embodiment of the present invention, there is provided a pharmaceutical composition for preventing or treating diseases which is beneficial for kinase inhibitory actions, comprising the compound represented by Chemical Formula 1, or a pharmaceutically acceptable salt, hydrate, solvate or isomer thereof as an active ingredient.

In this case, the diseases which is associated with kinase inhibitory actions includes inflammatory diseases, autoimmune diseases, proliferative diseases or hyperproliferative diseases, and immunity mediated diseases, cancers, tumors or the like.

The term "prevention" as used herein refers to any act to delay or inhibit occurrence, spread or recurrence of the above-mentioned diseases by administration of the composition of the present invention, and the term "treatment" as used herein refers to any act to improve or change the symptoms of the above diseases for the better by administration of the composition of the present invention.

The pharmaceutical composition of the present invention can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like, but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

Pharmaceutical dosage forms of the compounds of the present invention may include using the compounds in the form of pharmaceutically acceptable salts or solvates thereof, and using the compounds alone or as a combination and/or a suitable mixture together with other pharmaceutically active compounds.

The compounds of the present invention can be formulated into injection solutions by dissolving, suspending or emulsifying the compounds in a water-soluble solvent such as normal saline, 5% dextrose or a non-aqueous solvent such as synthetic fatty acid glyceride, higher fatty acid ester or propylene glycol. Formulations of the present invention may include conventional additives such as solubilizers, isotonic agents, suspending agents, emulsifying agents, stabilizers and preservatives.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administered daily at a dose of 0.0001 to 100 mg/kg (body weight), and preferably 0.001 to 100 mg/kg (body weight). The administration may be performed once a day or in divided doses each day through an oral or parenteral route. Depending on the method of administration, the composition may contain the compound of the present invention in an amount of 0.001 to 99% by weight, preferably 0.01 to 60% by weight.

The pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present invention or a pharmaceutically acceptable salt, hydrate, solvate or isomer thereof can be usefully used for the prevention or treatment of diseases which are associated with kinase inhibitory actions.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

Example 1: Preparation of 1-((3S,4R)-3-(5-chloro-2-(1-ethyl-1H-pyrazol-4-ylamino)-7H-pyrrolo[2,3-d]pyrimidin-4-ylamino)-4-fluoropiperidin-1-yl)prop-2-en-1-one

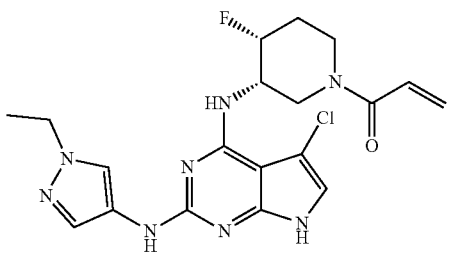 [SMILES: C=CC(=O)N1CC[C@@H](F)[C@@H](Nc2nc(Nc3cnn(CC)c3)nc3[nH]cc(Cl)c23)C1]

Step 1: Preparation of tert-butyl (3S,4R)-3-((2,5-dichloro-7H-pyrrolo[2,3-d]pyrimidin-4-yl)amino)-4-fluoropiperidine-1-carboxylate After 2,4,5-trichloro-7H-pyrrolo [2,3-d] pyrimidine (2.0 g, 9.0 mmol) was dissolved in ethanol (10.0 mL), N,N-diisopropylethylamine (4.8 mL, 28.0 mmol) and tert-butyl (3S,4R)-3-amino-4-fluoropiperidine-1-carboxylate (2.0 g, 9.0 mmol) were added thereto. The reaction mixture was stirred at 110° C. for 24 hours. After adding ethyl acetate, distilled water was added and the organic layer was separated. The separated organic layer was treated with sodium sulfate, filtered and concentrated under reduced pressure. The residue was separated by column chromatography to obtain 1.8 g (yield: 45.9%) of the title compound.

1H NMR (500 MHz, $CD_3OD$) δ 7.12 (s, 1H), 6.35-6.33 (m, 1H), 5.08-4.98 (m, 1H), 4.52-4.49 (m, 1H), 4.02-4.00 (m, 1H), 3.75-3.73 (m, 1H), 3.44-3.42 (m, 1H), 2.09-1.46 (m, 2H), 1.41 (s, 9H)

Step 2: Preparation of 2,5-dichloro-N-((3S,4R)-4-fluoropiperidin-3-yl)-7H-pyrrolo[2,3-d]pyrimidin-4-amine 6N hydrochloric acid solution (180.0 mL, excess) dissolved in methanol was added to tert-butyl (3S,4R)-3-((2,5-dichloro-7H-pyrrolo[2,3-d]pynmidin-4-yl)amino)-4-fluoropiperidine-1-carboxylate (1.8 g, 4.4 mmol). After stirring at room temperature for 30 minutes, the reaction solution was concentrated and then the next reaction was carried out without separation.

Step 3: Preparation of 1-((3S,4R)-3-((2,5-dichloro-7H-pyrrolo[2,3-d]pyrimidin-4-yl)amino)-4-fluoropiperidine-1-yl)prop-2-en-1-one After 2,5-dichloro-N-((3S,4R)-4-fluoropiperidin-3-yl)-7H-pyrrolo[2,3-d]pyrmidin-4-amine (1.3 g, 4.0 mmol) and sodium bicarbonate (1.8 g, 22.0 mmol) was dissolved in tetrahydrofuran/distilled water (5.0 mL/1.0 mL), acryloyl chloride (355.0 uL, 4.0 mmol) was added thereto at 0° C. The reaction mixture was stirred at 0° C. for 1 hour. After adding ethyl acetate, distilled water was added and the organic layer was separated. The separated organic layer was treated with sodium sulfate, filtered and concentrated under reduced pressure. The residue was separated by column chromatography to obtain 1.1 mg (yield: 67.5%) of the title compound.

1H NMR (500 MHz, CD$_3$OD) δ 7.14 (s, 1H), 6.92-6.87 (m, 1H), 6.25-6.22 (m, 1H), 5.78-5.76 (m, 1H), 5.17-5.03 (m, 1H), 4.60-4.28 (m, 3H), 3.49-3.44 (m, 1H), 3.23-3.20 (m, 1H), 2.17-2.15 (m, 1H), 2.01-1.94 (m, 1H)

Step 4: Preparation of 1-((3S,4R)-3-(5-chloro-2-(1-ethyl-1H-pyrazol-4-ylamino)-7H-pyrrolo[2,3-d]pyrimidin-4-ylamino)-4-fluoropiperidin-1-yl)prop-2-en-1-one 1-((3S,4R)-3-((2,5-dichloro-7H-pyrrolo[2,3-d]pyrimidin-4-yl)amino)-4-fluoropiperidine-1-yl)prop-2-en-1-one (1.0 g, 2.8 mmol) and 1-ethyl-1H-pyrazol-4-amine (238.7 mg, 2.1 mmol) were dissolved in 2-butanol (10.0 mL). After adding trifluoroacetic acid (197.3 mL, 2.6 mmol), the reaction mixture was reacted at 110° C. for 12 hours, and then the solvent was concentrated. The reaction product was neutralized by adding a 7N ammonia solution dissolved in methanol, and the residue was separated by column chromatography to obtain 179.0 mg (yield: 19.3%) of the title compound.

1H NMR (500 MHz, CD$_3$OD) δ 7.96-7.91 (m, 1H), 7.53-7.48 (m, 1H), 6.84-6.62 (m, 2H), 6.30-6.14 (m, 1H), 5.81-5.61 (m, 1H), 5.12-5.02 (m, 1H), 4.55-4.41 (m, 1H), 4.24-4.01 (m, 4H), 3.53-3.41 (m, 1H), 3.25-2.95 (m, 1H), 2.20-2.17 (m, 1H), 1.99-1.84 (m, 1H), 1.44-1.39 (m, 3H)

Example 2: Preparation of 1-((3S,4R)-3-(5-chloro-2-(1-(2,2-difluoroethyl)-1H-pyrazol-4-ylamino)-7H-pyrrolo[2,3-d]pyrimidin-4-ylamino)-4-fluoropiperidin-1-yl)prop-2-en-1-one

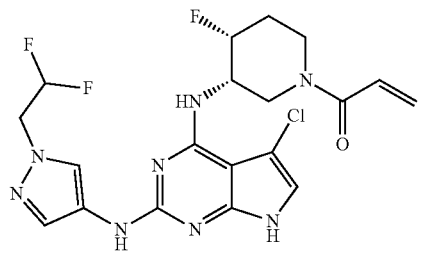 [SMILES: C=CC(=O)N1CC[C@@H](F)[C@@H](Nc2nc(Nc3cnn(CC(F)F)c3)nc3[nH]cc(Cl)c23)C1]

29.3 mg (yield: 57.1%) of the title compound was obtained in the same manner as in Example 1, except that 1-(2,2-difluoroethyl)-1H-pyrazol-4-amine was used instead of 1-ethyl-1H-pyrazol-4-amine in Example 1.

1H NMR (500 MHz, CD$_3$OD) δ 8.10-7.99 (m, 1H), 7.62-7.51 (m, 1H), 6.84-6.61 (m, 2H), 6.29-6.13 (m, 1H), 5.82-5.60 (m, 1H), 5.12-5.02 (m, 1H), 4.55-4.41 (m, 3H), 4.23-4.02 (m, 1H), 3.52-3.40 (m, 1H), 3.26-2.95 (m, 1H), 2.22-2.11 (m, 1H), 1.99-1.86 (m, 1H), 1.32-1.28 (m, 2H)

Example 3: Preparation of 1-((3S,4R)-3-(5-chloro-2-(1-cyclopropyl-1H-pyrazol-4-ylamino)-7H-pyrrolo[2,3-d]pyrimidin-4-ylamino)-4-fluoropiperidin-1-yl)prop-2-en-1-one

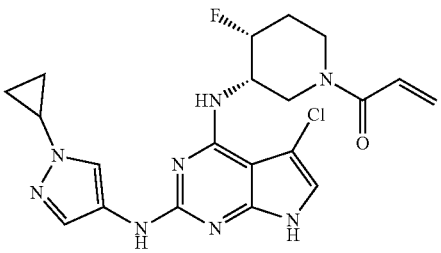 [SMILES: C=CC(=O)N1CC[C@@H](F)[C@@H](Nc2nc(Nc3cnn(C4CC4)c3)nc3[nH]cc(Cl)c23)C1]

7.3 mg (yield: 13.3%) of the title compound was obtained in the same manner as in Example 1, except that 1-cyclopropyl-1H-pyrazol-4-amine was used instead of 1-ethyl-1H-pyrazol-4-amine in Example 1.

1H NMR (500 MHz, CD$_3$OD) δ 7.99-7.96 (m, 1H), 7.50-7.48 (m, 1H), 6.85-6.61 (m, 2H), 6.29-6.15 (m, 1H), 5.81-5.63 (m, 1H), 5.14-5.04 (m, 1H), 4.58-4.42 (m, 1H), 4.27-4.01 (m, 1H), 3.57-3.46 (m, 2H), 3.26-2.97 (m, 1H), 2.20-2.17 (m, 1H), 2.01-1.98 (m, 1H), 1.94-1.60 (m, 1H), 1.04-0.89 (m, 4H)

Example 4: Preparation of 1-((3S,4R)-3-(5-chloro-2-(isoxazol-4-ylamino)-7H-pyrrolo[2,3-d]pyrimidin-4-ylamino)-4-fluoropiperidin-1-yl)prop-2-en-1-one

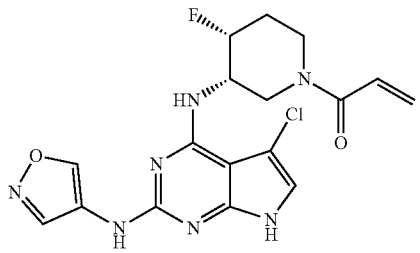 [SMILES: C=CC(=O)N1CC[C@@H](F)[C@@H](Nc2nc(Nc3cnoc3)nc3[nH]cc(Cl)c23)C1]

18.7 mg (yield: 24.1%) of the title compound was obtained in the same manner as in Example 1, except that isooxazole-4-amine was used instead of 1-ethyl-1H-pyrazol-4-amine in Example 1.

1H NMR (500 MHz, CD$_3$OD) δ 9.08-8.99 (m, 1H), 8.51-8.40 (m, 1H), 6.89-6.66 (m, 2H), 6.33-6.09 (m, 1H), 5.85-5.60 (m, 1H), 5.15-4.98 (m, 1H), 4.62-4.28 (m, 1H), 4.27-3.96 (m, 2H), 3.58-3.38 (m, 1H), 3.09-2.65 (m, 1H), 2.25-2.08 (m, 1H), 1.97-1.78 (m, 1H)

Example 5: Preparation of 1-((3S,4R)-3-(5-chloro-2-(isothiazol-4-ylamino)-7H-pyrrolo[2,3-d]pyrimidin-4-ylamino)-4-fluoropiperidin-1-yl)prop-2-en-1-one

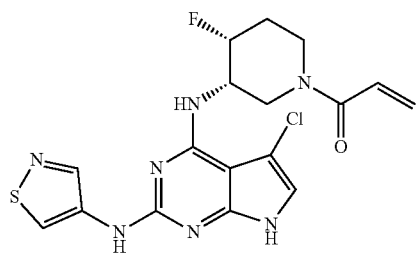 [SMILES: C=CC(=O)N1CC[C@@H](F)[C@@H](Nc2nc(Nc3cnsc3)nc3[nH]cc(Cl)c23)C1]

7.3 mg (yield: 40.3%) of the title compound was obtained in the same manner as in Example 1, except that isothiazol-4-amine was used instead of 1-ethyl-1H-pyrazol-4-amine in Example 1.

1H NMR (500 MHz, CD$_3$OD) δ 9.00-8.85 (m, 1H), 8.65-8.55 (m, 1H), 7.15-6.65 (m, 2H), 6.35-6.10 (m, 1H), 5.85-5.60 (m, 1H), 5.20-5.05 (m, 1H), 4.65-4.00 (m, 3H), 3.60-3.40 (m, 1H), 3.10-3.00 (m, 1H), 2.10-1.90 (m, 1H), 1.65-1.55 (m, 1H)

Example 6: Preparation of 4-((3S,4R)-1-acryloyl-4-fluoropiperidin-3-ylamino)-2-(1-ethyl-1H-pyrazol-4-ylamino)-7H-pyrrolo[2,3-d]pyrimidine-5-carbonitrile

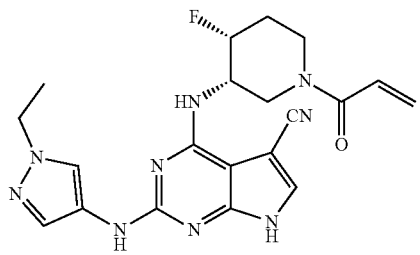 [SMILES: C=CC(=O)N1CC[C@@H](F)[C@@H](Nc2nc(Nc3cnn(CC)c3)nc3[nH]cc(C#N)c23)C1]

2.8 mg (yield: 23.1%) of the title compound was obtained in the same manner as in Example 1, except that 2,4-dichloro-7H-pyrrolo[2,3-d]pynmidine-5-carbonitrile was instead of 2,4,5-trichloro-7H-pyrrolo[2,3-d]pyrmidine in Example 1.

1H NMR (500 MHz, CD$_3$OD) δ 8.00-7.90 (m, 1H), 7.60-7.50 (m, 2H), 6.90-6.60 (m, 1H), 6.30-6.10 (m, 1H), 5.82-5.60 (m, 1H), 5.20-5.00 (m, 1H), 4.60-4.45 (m, 1H), 4.30-4.00 (m, 3H), 3.60-3.40 (m, 1H), 2.25-2.10 (m, 1H), 2.08-1.85 (m, 2H), 1.63-1.52 (m, 1H), 1.45-1.38 (m, 3H)

Example 7: Preparation of 4-((3S,4R)-1-acryloyl-4-fluoropiperidin-3-ylamino)-2-(1-(2,2-difluoroethyl)-1H-pyrazol-4-ylamino)-7H-pyrrolo[2,3-d]pyrimidine-5-carbonitrle

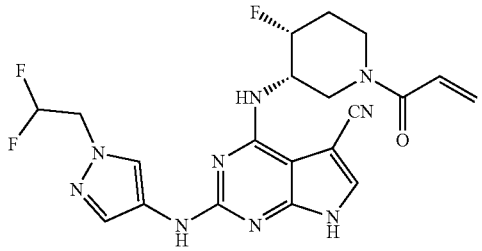 [SMILES: C=CC(=O)N1CC[C@@H](F)[C@@H](Nc2nc(Nc3cnn(CC(F)F)c3)nc3[nH]cc(C#N)c23)C1]

5.6 mg (yield: 42.4%) of the title compound was obtained in the same manner as in Example 1, except that 2,4-dichloro-7H-pyrrolo[2,3-d]pynmidine-5-carbonitrile was instead of 2,4,5-trichloro-7H-pyrrolo[2,3-d]pyrmidine, and 1-(2,2-difluoroethyl)-1H-pyrazol-4-amine was used instead of 1-ethyl-1H-pyrazol-4-amine in Example 1.

1H NMR (500 MHz, CD$_3$OD) δ 8.17-7.97 (m, 1H), 7.70-7.50 (m, 2H), 6.90-6.60 (m, 1H), 6.33-5.98 (m, 2H), 5.82-5.60 (m, 1H), 5.20-5.00 (m, 1H), 4.60-4.40 (m, 3H), 4.30-3.00 (m, 3H), 2.25-2.10 (m, 1H), 2.02-1.85 (m, 1H), 1.65-1.50 (m, 1H)

Example 8: Preparation of 4-((3S,4R)-1-acryloyl-4-fluoropiperidin-3-ylamino)-2-(1-cyclopropyl-1H-pyrazol-4-ylamino)-7H-pyrrolo[2,3-d]pyrimidine-5-carbonitrle

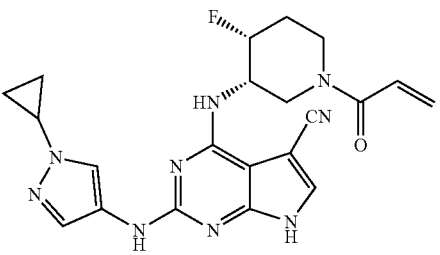 [SMILES: C=CC(=O)N1CC[C@@H](F)[C@@H](Nc2nc(Nc3cnn(C4CC4)c3)nc3[nH]cc(C#N)c23)C1]

4.1 mg (yield: 32.8%) of the title compound was obtained in the same manner as in Example 1, except that 2,4-dichloro-7H-pyrrolo[2,3-d]pynmidine-5-carbonitrile was instead of 2,4,5-trichloro-7H-pyrrolo[2,3-d]pyrmidine, and 1-cydopropyl-1H-pyrazol-4-amine was used instead of 1-ethyl-1H-pyrazol-4-amine in Example 1.

1H NMR (500 MHz, CD$_3$OD) δ 8.05-7.97 (m, 1H), 7.60-7.50 (m, 2H), 6.90-6.60 (m, 1H), 6.30-6.10 (m, 1H), 5.82-5.60 (m, 1H), 5.20-5.00 (m, 1H), 4.62-4.40 (m, 1H), 4.30-4.00 (m, 1H), 3.60-3.30 (m, 2H), 3.10-3.00 (m, 1H), 2.30-2.10 (m, 1H), 2.05-1.95 (m, 1H), 1.65-1.55 (m, 1H), 1.08-0.93 (m, 4H)

Example 9: Preparation of 4-((3S,4R)-1-acryloyl-4-fluoropiperidin-3-ylamino)-2-(isoxazol-4-ylamino)-7H-pyrrolo[2,3-d]pyrimidine-5-carbonitrle

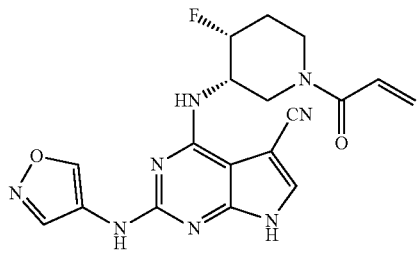 [SMILES: C=CC(=O)N1CC[C@@H](F)[C@@H](Nc2nc(Nc3cnoc3)nc3[nH]cc(C#N)c23)C1]

11.5 mg (yield: 12.2%) of the title compound was obtained in the same manner as in Example 1, except that 2,4-dichloro-7H-pyrrolo[2,3-d]pynmidine-5-carbonitrile was instead of 2,4,5-trichloro-7H-pyrrolo[2,3-d]pynmidine, and isooxazole-4-amine was used instead of 1-ethyl-1H-pyrazol-4-amine in Example 1.

1H NMR (500 MHz, CD$_3$OD) δ 9.10-9.00 (m, 1H), 8.50-8.40 (m, 1H), 7.63-7.55 (m, 1H), 6.90-6.65 (m, 1H), 6.30-6.10 (m, 1H), 5.85-5.60 (m, 1H), 5.20-5.05 (m, 1H), 4.65-4.00 (m, 3H), 3.65-3.00 (m, 2H), 2.10-1.90 (m, 1H), 1.65-1.50 (m, 1H)

Example 10: Preparation of 1-((3S,4R)-3-(2-(1-ethyl-1H-pyrazol-4-ylamino)-5-methyl-7H-pyrrolo[2,3-d]pyrimidin-4-ylamino)-4-fluoropiperidin-1-yl)prop-2-en-1-one

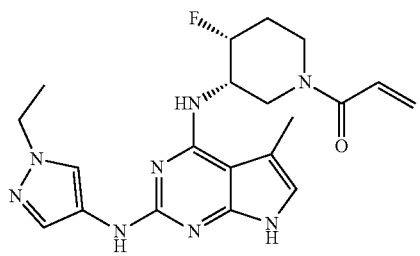 [SMILES: C=CC(=O)N1CC[C@@H](F)[C@@H](Nc2nc(Nc3cnn(CC)c3)nc3[nH]cc(C)c23)C1]

13.8 mg (yield: 41.4%) of the title compound was obtained in the same manner as in Example 1, except that 2,4-dichloro-5-methyl-7H-pyrrolo[2,3-d]pyrmidine was instead of 2,4,5-trichloro-7H-pyrrolo[2,3-d]pyrimidine in Example 1.

1H NMR (500 MHz, CD$_3$OD) δ 8.00-7.85 (m, 1H), 7.50-7.40 (m, 1H), 6.90-6.60 (m, 1H), 6.52 (s, 1H), 6.33-6.13 (m, 1H), 5.85-5.60 (m, 1H), 5.20-5.02 (m, 1H), 4.55-4.40 (m, 1H), 4.15-4.00 (m, 3H), 3.55-3.40 (m, 1H), 3.30-2.98 (m, 1H), 2.40-2.30 (m, 3H), 2.25-1.55 (m, 3H), 1.45-1.32 (m, 3H)

Example 11: Preparation of 1-((3S,4R)-4-fluoro-3-(2-(isoxazol-4-ylamino)-5-methyl-7H-pyrrolo[2,3-d]pyrimidin-4-ylamino)piperidin-1-yl)prop-2-en-1-one

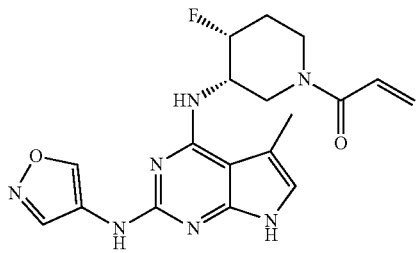 [SMILES: C=CC(=O)N1CC[C@@H](F)[C@@H](Nc2nc(Nc3cnoc3)nc3[nH]cc(C)c23)C1]

10.4 mg (yield: 13.5%) of the title compound was obtained in the same manner as in Example 1, except that 2,4-dichloro-5-methyl-7H-pyrrolo[2,3-d]pyrimidine was instead of 2,4,5-trichloro-7H-pyrrolo[2,3-d]pyrimidine, and isooxazol-4-amine was used instead of 1-ethyl-1H-pyrazol-4-amine in Example 1.

1H NMR (500 MHz, CD$_3$OD) δ 9.10-9.00 (m, 1H), 8.50-8.40 (m, 1H), 6.95-6.68 (m, 1H), 6.60-6.52 (m, 1H), 6.33-6.13 (m, 1H), 5.85-5.60 (m, 1H), 5.20-5.02 (m, 1H), 4.55-4.40 (m, 1H), 4.35-4.00 (m, 2H), 3.60-3.40 (m, 1H), 3.10-3.00 (m, 1H), 2.36 (s, 3H), 2.10-1.95 (m, 2H)

Example 12: Preparation of 1-((3S,4S)-3-(5-chloro-2-(1-ethyl-1H-pyrazol-4-ylamino)-7H-pyrrolo[2,3-d]pyrimidin-4-ylamino)-4-fluoropiperidin-1-yl)prop-2-en-1-one

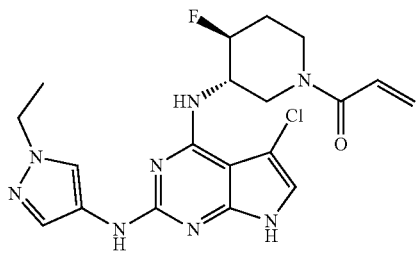 [SMILES: C=CC(=O)N1CC[C@H](F)[C@@H](Nc2nc(Nc3cnn(CC)c3)nc3[nH]cc(Cl)c23)C1]

14.4 mg (yield: 15.5%) of the title compound was obtained in the same manner as in Example 1, except that tert-butyl(3S,4S)-3-amino-4-fluoropiperidine-1-carboxylate was used instead of tert-butyl(3S,4R)-3-amino-4-fluoropiperidine-1-carboxylate in Example 1.

1H NMR (500 MHz, CD$_3$OD) δ 7.95-7.88 (m, 1H), 7.55-7.48 (m, 1H), 6.88-6.60 (m, 2H), 6.30-6.15 (m, 1H), 5.85-5.60 (m, 1H), 5.15-4.97 (m, 1H), 4.60-4.35 (m, 1H), 4.15-4.05 (m, 2H), 4.04-3.92 (m, 1H), 3.90-3.65 (m, 2H), 2.20-1.80 (m, 3H), 1.48-1.35 (m, 3H)

Experimental Example 1: Measurement of Inhibitory Activity Against JAK3 and BTK Enzymes JAK3 and BTK kinases inhibitory activities were measured for the compounds prepared in the Examples through in vitro analysis on the ADP Glow (Glo) platform.

Specifically, the inhibitory activities against JAK3 and BTK kinase were measured using a JAK3 kinase assay kit (Promega, V9441) and a BTK kinase assay kit (Promega, V9071) which were purchased from Promega. Recombinant purified human JAK3 and BTK were diluted with 1× kinase reaction buffer (JAK3: 40 mM Tris-Cl, pH 7.5, 20 mM MgCl$_2$, 0.1 mg/mL BSA and 50 uM DTT/BTK: 40 mM Tris-Cl, pH 7.5, 20 mM MgCl$_2$, 0.1 mg/mL BSA, 2 mM MnCl$_2$ and 50 uM DTT) and added to 96 well plates (JAK3: final concentration of 4 ng per reaction/BTK: final concentration of 8 ng per reaction). The compounds prepared in the previous Examples were treated so as to be finally a 1% DMSO aqueous solution, and a substrate cocktail containing ATP (JAK3: final concentration of 5 uM/BTK: final concentration of 10 uM) and 0.2 ug/uL of Poly(Glu4, Tyr1) peptide (JAK3 and BTK final concentration) in the total 25 uL reactants was added to 96-well plates to initiate enzymatic reaction. After incubation (30° C.) for 1 hour, equivalent volume (25 uL per reaction) of ADP Glo was added and incubated (30° C.) for 40 minutes at room temperature. Then, a kinase detection reagent (50 uL per reaction) was added and incubated (30° C.) for 30 minutes at room temperature. The kinase activity was measured by chemiluminescence according to the instructions of ADP Glo kinase assay kit, and the inhibitory activity of the compounds according to the present invention was calculated. For the analysis of the results of each compound, Microsoft Excel was used, and IC$_{50}$ values were calculated by Sigma-Plot software. The results are shown in Table 1 below. Further, for comparison, Tofacitinib and Ibrutinib were evaluated in a similar way.

TABLE 1

| Example No. | JAK3 IC$_{50}$ (nM) | BTK IC$_{50}$ (nM) |
|---|---|---|
| 1 | 0.1 | 0.6 |
| 2 | 0.1 | 0.8 |
| 3 | 0.1 | 0.8 |
| 4 | 0.2 | 3.2 |
| 5 | 0.6 | 3.9 |
| 6 | 0.2 | 0.9 |
| 7 | 0.2 | 0.8 |
| 8 | 0.3 | 0.9 |
| 9 | 0.3 | 2.2 |
| 10 | 0.5 | 3.3 |
| 11 | 0.7 | 9.1 |
| 12 | 0.2 | 1.0 |
| Tofacitinib | 3.3 | — |
| Ibrutinib | — | 0.7 |

Experimental Example 2: JAK3-Mediated Cell Assay (HT-2/IL-2 Assay)

The inhibitory activities against JAK3 kinase at the cellular level were measured for the compounds prepared in the Examples through in vitro analysis of STAT5 phosphorylation induced by IL-2 stimulation in HT-2 cells. Specifically, STAT5 phosphorylation was analyzed using HTRF®phospho-STAT5 (Tyr694) assay kit (Cisbio, 64AT5PEG), which was purchased from Cisbio. HT-2 cells were cultured for 2 hours in growth factor-free medium. The cultured HT-2 cells were dispensed into 96-well plates by 50 ul so as to be a density of 2.5×10$^5$ cells/well. The compounds prepared in the previous Examples were prepared so as to be finally a 0.3% DMSO aqueous solution, and HT-2 cells was treated with the compounds for 30 minutes. After the compound treatment, IL-2 was prepared so as to be finally a concentration of 20 ng/ml, and HT-2 cells was treated for 10 minutes. The cells were then disrupted by treating lysis buffers for 30 minutes. The level of STAT5 phosphorylation was measured according to the instructions of HTRF® phospho-STAT5 assay kit, and the inhibitory activity of the compounds according to the invention was calculated. For the analysis of the results of each compound, Microsoft Excel was used, and IC$_{50}$ values were calculated by Sigma-Plot software.

TABLE 2

| Example No. | JAK3 Cell IC$_{50}$ (nM) |
|---|---|
| 1 | 30.9 |
| 2 | 49 |
| 4 | 51.8 |
| 5 | 288.3 |
| 9 | 282.0 |
| 10 | 241.5 |
| 11 | 248 |
| 12 | 25.4 |

The invention claimed is:
1. A compound represented by the following Chemical Formula 1, or a pharmaceutically acceptable salt thereof:

[Chemical Formula 1]

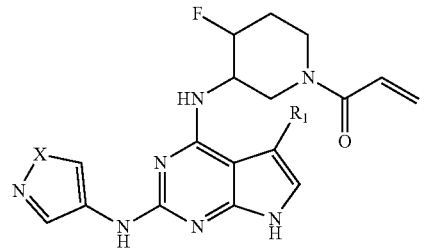

wherein, in Chemical Formula 1,
R$_1$ is C$_{1-5}$ alkyl, halogen, or cyano,
X is N—R$_2$, O, or S,
R$_2$ is C$_{1-5}$ alkyl, C$_{1-5}$ haloalkyl, or C$_{3-6}$ cycloalkyl.
2. The compound or a pharmaceutically acceptable salt thereof according to claim 1, wherein R$_1$ is methyl, ethyl, propyl, isopropyl, butyl, isobutyl, pentyl, isopentyl, neopentyl, bromo, chloro, fluoro, or cyano.
3. The compound or a pharmaceutically acceptable salt thereof according to claim 1, wherein R$_2$ is methyl, ethyl, propyl, isopropyl, butyl, isobutyl, pentyl, isopentyl, neopentyl, fluoromethyl, difluoromethyl, trifluoromethyl, 2-fluoroethyl, 2,2-difluoroethyl, 2,2,2-trifluoroethyl, cyclopropyl, cyclobutyl, cyclopentyl, or cyclohexyl.
4. The compound or a pharmaceutically acceptable salt thereof according to claim 1, wherein the compounds represented by the Chemical Formula 1 is any one selected from the group consisting of the following:
  1) 1-((3S,4R)-3-(5-chloro-2-(1-ethyl-1H-pyrazol-4-ylamino)-7H-pyrrolo[2,3-d]pyrimidin-4-ylamino)-4-fluoropiperidin-1-yl)prop-2-en-1-one,
  2) 1-((3S,4R)-3-(5-chloro-2-(1-(2,2-difluoroethyl)-1H-pyrazol-4-ylamino)-7H-pyrrolo[2,3-d]pyrimidin-4-ylamino)-4-fluoropiperidin-1-yl)prop-2-en-1-one,
  3) 1-((3S,4R)-3-(5-chloro-2-(1-cyclopropyl-1H-pyrazol-4-ylamino)-7H-pyrrolo[2,3-d]pyrimidin-4-ylamino)-4-fluoropiperidin-1-yl)prop-2-en-1-one,
  4) 1-((3S,4R)-3-(5-chloro-2-(isoxazol-4-ylamino)-7H-pyrrolo[2,3-d]pyrimidin-4-ylamino)-4-fluoropiperidin-1-yl)prop-2-en-1-one, 5) 1-((3S,4R)-3-(5-chloro-2-(isothiazol-4-ylamino)-7H-pyrrolo[2,3-d]pyrimidin-4-ylamino)-4-fluoropiperidin-1-yl)prop-2-en-1-one,
6) 4-((3S,4R)-1-acryloyl-4-fluoropiperidin-3-ylamino)-2-(1-ethyl-1H-pyrazol-4-ylamino)-7H-pyrrolo[2,3-d]pyrimidine-5-carbonitrile,
7) 4-((3S,4R)-1-acryloyl-4-fluoropiperidin-3-ylamino)-2-(1-(2,2-difluoroethyl)-1H-pyrazol-4-ylamino)-7H-pyrrolo[2,3-d]pyrimidine-5-carbonitrile,
8) 4-((3S,4R)-1-acryloyl-4-fluoropiperidin-3-ylamino)-2-(1-cyclopropyl-1H-pyrazol-4-ylamino)-7H-pyrrolo[2,3-d]pyrimidine-5-carbonitrile,
9) 4-((3S,4R)-1-acryloyl-4-fluoropiperidin-3-ylamino)-2-(isoxazol-4-ylamino)-7H-pyrrolo[2,3-d]pyrimidine-5-carbonitrile,
10) 1-((3S,4R)-3-(2-(1-ethyl-1H-pyrazol-4-ylamino)-5-methyl-7H-pyrrolo[2,3-d]pyrimidin-4-ylamino)-4-fluoropiperidin-1-yl)prop-2-en-1-one,
11) 1-((3S,4R)-4-fluoro-3-(2-(isoxazol-4-ylamino)-5-methyl-7H-pyrrolo[2,3-d]pyrimidin-4-ylamino)piperidin-1-yl)prop-2-en-1-one, and
12) 1-((3S,4S)-3-(5-chloro-2-(1-ethyl-1H-pyrazol-4-ylamino)-7H-pyrrolo[2,3-d]pyrimidin-4-ylamino)-4-fluoropiperidin-1-yl)prop-2-en-1-one.

5. A pharmaceutical composition comprising the compound according to claim 1 or a pharmaceutically acceptable salt thereof.

6. A method for inhibiting the activity of JAK3 and/or BTK comprising administering to a subject in need thereof an effective amount of the compound according to claim 1 or a pharmaceutically acceptable salt thereof.

\* \* \* \* \*